US00PP34123P2

(12) United States Plant Patent
Los et al.

(10) Patent No.: US PP34,123 P2
(45) Date of Patent: Apr. 12, 2022

(54) ***MANDEVILLA* PLANT NAMED 'PATMANROS5'**

(50) Latin Name: ***Mandevilla sanderi* (Hemsl.) Woodson.**
Varietal Denomination: PATMANROS5

(71) Applicant: Patio Plants V.O.F., Klazienaveen (NL)

(72) Inventors: Martijn Los, Klazienaveen (NL); Maurits van den Arend, Klazienaveen (NL)

(73) Assignee: Patio Plants V.O.F., Klazienaveen (NL)

( * ) Notice: Subject to any disclaimer, the term of this patent is extended or adjusted under 35 U.S.C. 154(b) by 0 days.

(21) Appl. No.: 17/300,788

(22) Filed: Nov. 9, 2021

(30) Foreign Application Priority Data

Nov. 27, 2020 (QZ) ..... PBR 2020/3041

(51) Int. Cl.
*A01H 5/02* (2018.01)
*A01H 6/08* (2018.01)

(52) U.S. Cl.
USPC ..... Plt./232

(58) Field of Classification Search
USPC ..... Plt./232
See application file for complete search history.

*Primary Examiner* — Susan McCormick Ewoldt
(74) *Attorney, Agent, or Firm* — Samuel R. McCoy, Jr.

(57) ABSTRACT

A new and distinct *Mandevilla* plant named 'PATMANROS5' which is characterized by an upright and freely branching growth habit, dark green and glossy foliage, very light red-purple flower buds, flowers with a very light red-purple outer corolla and a dark red-purple inner corolla, flower petals that are narrowly margined white, as well as the stability of these characteristics from generation to generation.

3 Drawing Sheets

Latin name of the genus and species: The Latin name of the genus and species of the novel variety disclosed herein is *Mandevilla sanderi* (Hemsl.) Woodson.

Variety denomination: The inventive variety of *Mandevilla* disclosed herein has been given the variety denomination 'PATMANROS5'.

CROSS REFERENCE TO RELATED APPLICATIONS

This application claims priority to the Community Plant Variety Rights application number 2020/3041, filed Nov. 27, 2020, which is herein incorporated by reference.

BACKGROUND OF THE INVENTION

Parentage: The new plant originated as a seedling selection from the open pollination of a plurality of cultivated *Mandevilla sanderi* unnamed *Mandevilla sanderi* plants (not patented) in the spring of 2017. The true parentage of the claimed plant is unknown. Seed was collected from a plurality of these openly-pollinated *Mandevilla sanderi* plants and germinated at a greenhouse in Klazienaveen, The Netherlands. The resulting seedlings were grown to maturity and observed for unique characteristics. In March of 2018, the claimed plant was observed to exhibit a darker pink flower color with a narrow white petal margin, whereas the parent and other seedlings did not from said cross of 2017 and was selected for commercialization.

Asexual Reproduction: Asexual reproduction of the new cultivar 'PATMANROS5', by way of softwood stem cuttings, was first initiated in March of 2018 in Klazienaveen, The Netherlands. Through more than 6 subsequent generations, the unique features of this cultivar have proven to be stable and true to type.

SUMMARY OF THE INVENTION

The cultivar 'PATMANROS5' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'PATMANROS5'. These characteristics in combination distinguish 'PATMANROS5' as a new and distinct *Mandevilla* cultivar:

1. *Mandevilla* 'PATMANROS5' exhibits an upright, freely branching growth habit; and
2. *Mandevilla* 'PATMANROS5' exhibits dark green, glossy foliage; and
3. *Mandevilla* 'PATMANROS5' exhibits very light red-purple flower buds which generally appear to be very light pink; and
4. *Mandevilla* 'PATMANROS5' exhibits flowers with a very light red-purple outer corolla, generally appearing as very light pink, which become progressively suffused with a darker shade of red-purple towards the apex of the petals; and
5. *Mandevilla* 'PATMANROS5' exhibits flowers with a red-purple inner corolla, generally appearing as deep pink, which are narrowly margined white.

BOTANICAL DESCRIPTION OF THE PLANT

Figure 1:
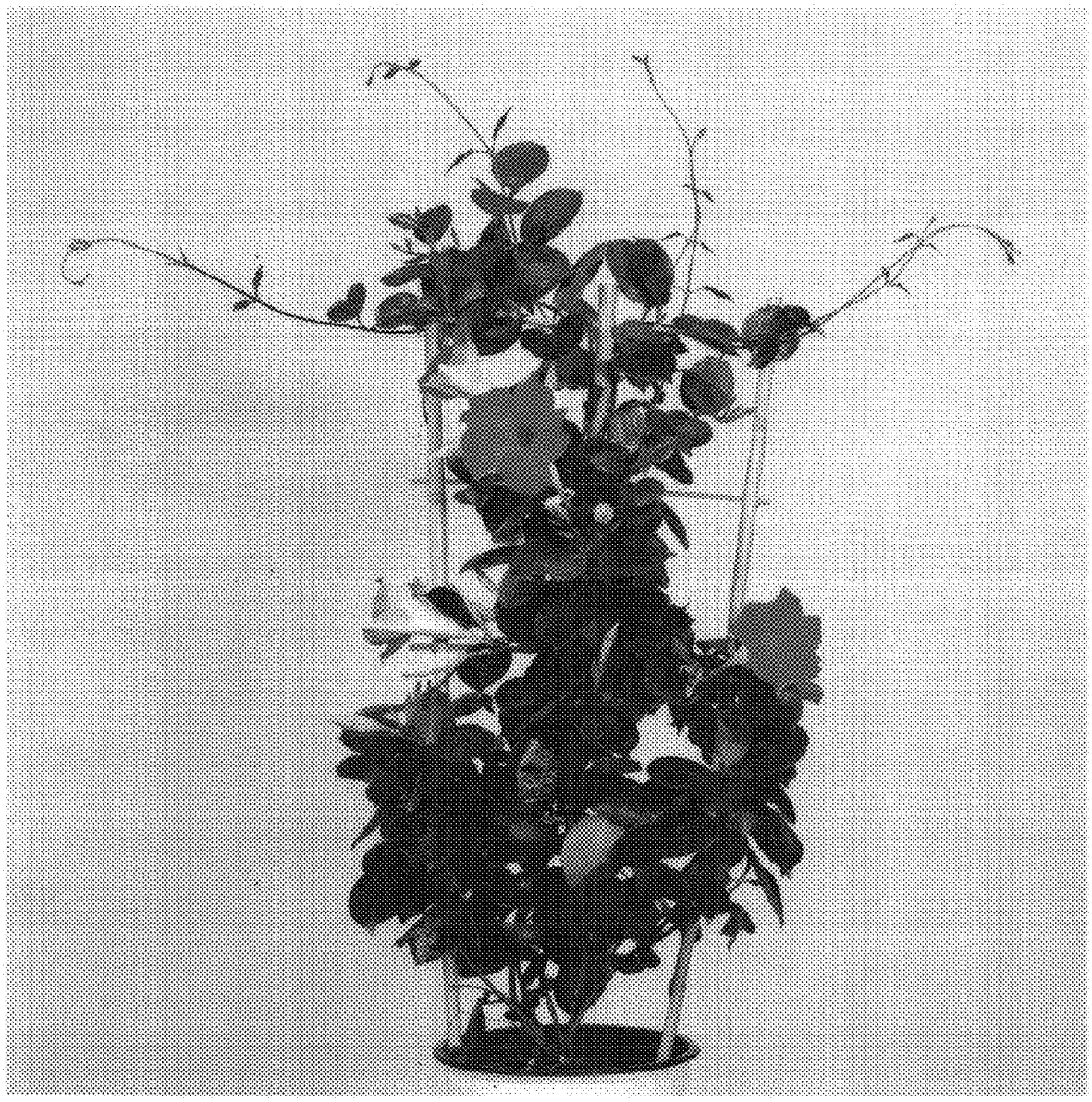
FIG. 1 illustrates, as nearly true as it is reasonably possible to make the same in color photographs of this type, an exemplary 12 month old 'PATMANROS5' plant in a 17 cm nursery pot, grown in a greenhouse in Klazienaveen, The Netherlands.
Figure 2:
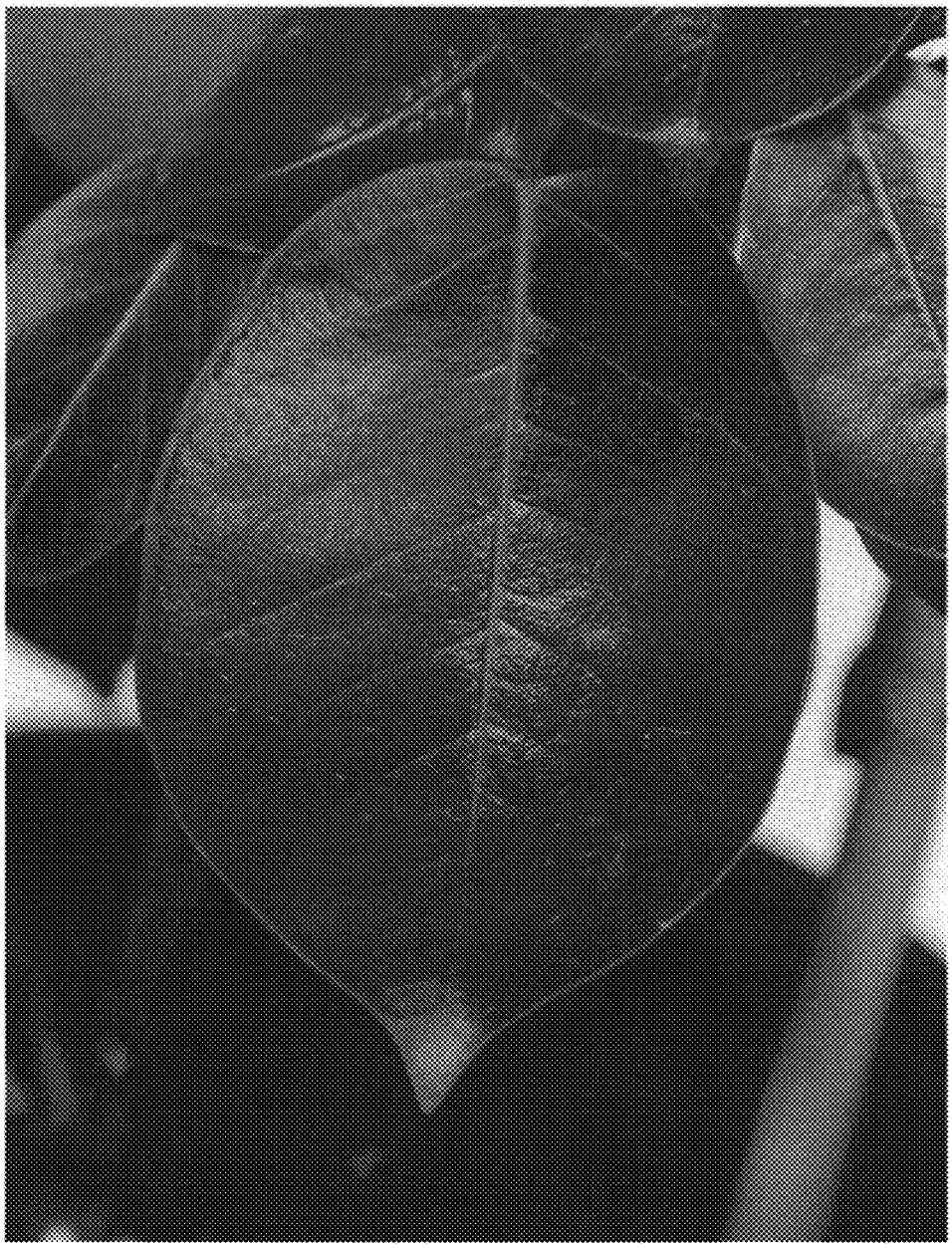
FIG. 2 illustrates, as nearly true as it is reasonably possible to make the same in color photographs of this type, the mature foliage of 'PATMANROS5'.
Figure 3:
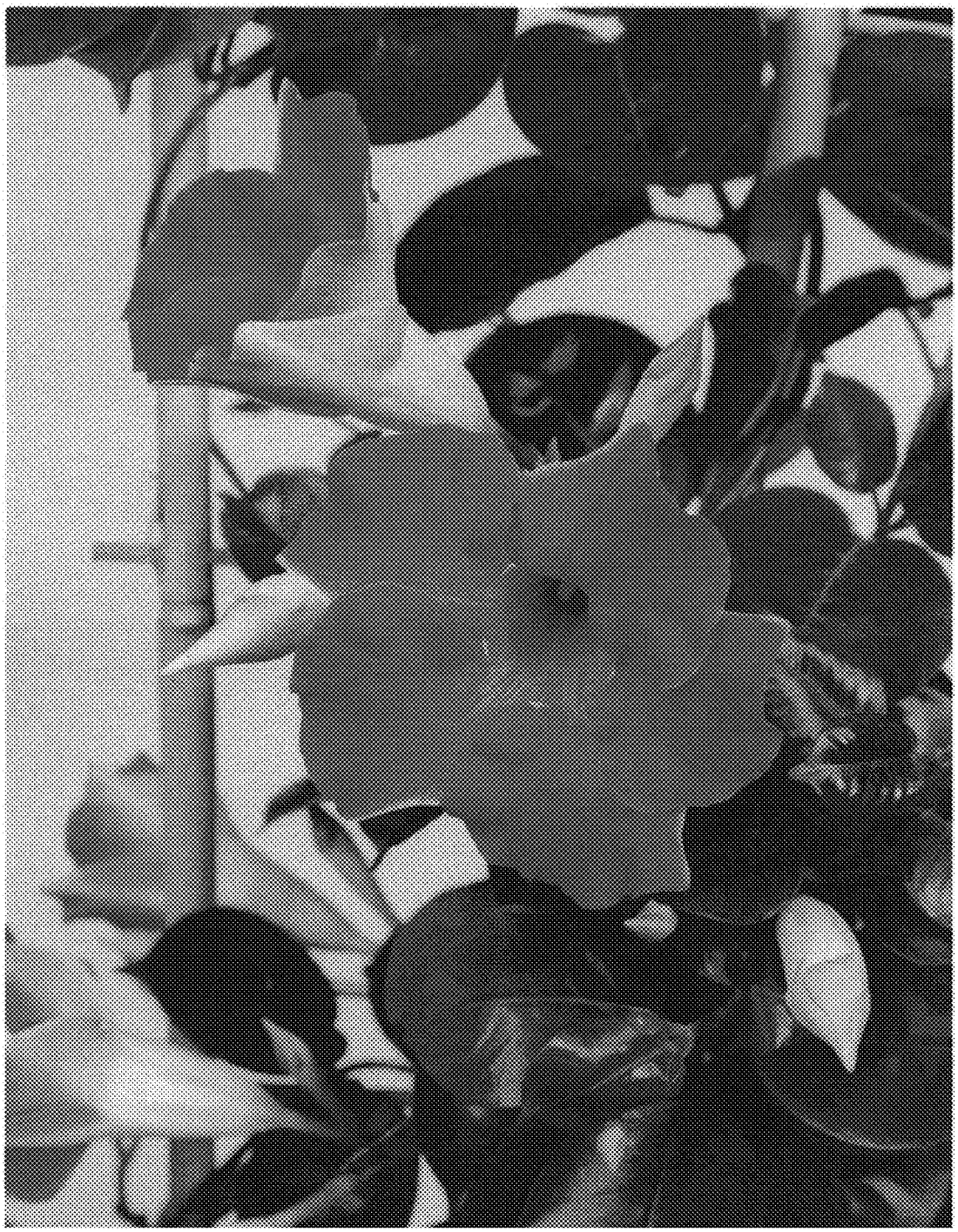
FIG. 3 illustrates, as nearly true as it is reasonably possible to make the same in color photographs of this type, an exemplary flower of 'PATMANROS5'.

The following observations and measurements were made in April of 2021 and describe averages from a sample set of six specimens of 12 month-old 'PATMANROS5' plants grown in 17 cm nursery pots grown in a greenhouse in Klazienaveen, The Netherlands. Plants were produced using conventional greenhouse production protocols for *Mandevilla* which consisted of regular overhead and ebb and flood irrigation and fertigation applications. Pest or disease control measures were utilized in production as required. Plants were produced with full sun exposure and no photoperiodic treatments or artificial light was given to the plants.

Those skilled in the art will appreciate that certain characteristics will vary with older or, conversely, with younger plants. 'PATMANROS5' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2015 (sixth edition).

A botanical description of 'PATMANROS5' and comparisons with the most similar commercial variety of *Mandevilla* is provided below.

Plant description:

*Growth habit*.—Vining perennial; broad upright.

*Plant shape*.—Obovate to broad obovate.

*Average height from base to top of foliage*.—75.2 cm.

*Average height from base to top of the floral plane*.—52.0 cm.

*Average width*.—42.5 cm.

*Growth rate*.—Moderately fast growing.

*Plant vigor*.—Moderately vigorous to vigorous.

*Propagation method*.—Softwood stem cuttings; rooting is in initiated in approximately 21 days, with a fully rooted cutting in approximately 6 weeks, when grown in a greenhouse with an ambient average temperature of 28 to 30 degrees Celsius.

*Time to produce a finished plant*.—Approximately 9 to 12 months is required to produce a fully rooted and marketable 19 cm plant when grown under greenhouse conditions.

*Disease and pest resistance or susceptibility*.—Plants have not been observed to be susceptible or resistant to pathogens and pests common to *Mandevilla sanderi*.

*Environmental tolerances*.—Adapt to at least USDA Zones 10 and 12, and temperatures ranging from at least 5 degrees to 40 degrees Celsius; moderate tolerance to rain; low to moderate tolerance to wind; low tolerance to drought.

Root system:

*General*.—Freely branching; moderately dense rooting.

*Texture*.—Fibrous.

*Color*.—Light brown.

Stem:

*Branching habit*.—Basally branching main stem; freely branching with lateral branches. Stems and branches exude a milky exudate when damaged.

*Number of main stems per plant*.—6.

*Number of lateral branches per plant*.—4.

*Aspect; cross-section*.—Rounded.

*Length of lateral branches*.—26.2 cm.

*Diameter of lateral branches*.—0.25 cm at the widest point.

*Internode length on lateral branches*.—6.0 cm.

*Attitude*.—Outward; angle is approximately 50 degrees from vertical.

*Strength*.—Strong.

*Texture and luster*.—Glabrous and moderately glossy.

*Color, juvenile*.—Greyed-brown, nearest to a mixture of RHS N199B and N199C, and suffused with green, nearest to RHS 152A yet darker.

*Color, mature*.—Yellow-green, nearest to a mixture of RHS 144A and 144B.

*Color at internodes*.—Yellow-green, nearest to a mixture of RHS 144A and 144B.

*Color of bark on main stems*.—Brown, nearest to RHS 200D.

Foliage:

*Arrangement*.—Opposite.

*Division*.—Simple.

*Quantity*.—Average of 10 leaves per lateral branch.

*Lamina*.—Dimensions — 7.0 cm long and 5.2 cm wide, on average. Shape — Broad obovate to broad elliptic. Aspect — Flat to slightly concave or slightly convex. Apex — Abruptly acute. Base — Obtuse to truncate. Margin — Entire; not undulated. Pubescence, texture and luster of adaxial surface — Glabrous, smooth, and glossy. Pubescence, texture and luster of abaxial surface — Glabrous, smooth, and slightly glossy. Color — Juvenile foliage, adaxial surface — Green, nearest to RHS NN137A, and lightly suffused with yellow-green, nearest to RHS 146A. Juvenile foliage, abaxial surface — Greyed-brown, nearest to RHS N199A. Mature foliage, adaxial surface — Nearest to in between yellow-green and greyed-green; RHS 147A and N189A yet darker. Mature foliage, abaxial surface — Yellow-green, nearest to RHS 146B. Venation — Pattern — Pinnate. Venation color, adaxial surface — Green, nearest to RHS 143C. Venation color, abaxial surface — Yellow-green, nearest to in between RHS 145C and 150D.

*Petiole*.—Length — 1.4 cm. Width — 0.225 cm. Texture — Smooth and glabrous. Luster — Moderately glossy. Strength — Moderately strong. Color, adaxial surface — Yellow-green, nearest to RHS 152A. Color, abaxial surface — Yellow-green, nearest to RHS 144C.

Inflorescence:

*Inflorescence arrangement*.—Axillary raceme.

*Natural flowering season*.—Spring through autumn in USDA Hardiness Zones 10 through 12.

*Time to flower.*—Approximately 10 weeks from planting a rooted cutting.

*Dimensions.*—15.0 cm high and 12.4 cm in diameter.

*Quantity of flowers per inflorescence.*—5 on average; varying from 3 to 7.

*Quantity of flowers per plant.*—6.

*Quantity of flower buds per plant.*—60.

*Quantity of flowers and flower buds per plant.*—66.

*Peduncle.*—Dimensions — 6.9 cm long and 0.2 cm in diameter. Aspect — Upward and outward; at approximately 45 degrees to the lateral branch axis. Strength — Moderately strong. Texture and luster — Glabrous and moderately glossy. Color — Green, nearest to RHS 143C.

Bud:

*Shape.*—Oblanceolate.

*Dimensions.*—5.4 cm long and 0.9 cm in diameter.

*Pubescence, texture and luster.*—Glabrous, smooth and slightly glossy.

*Color.*—The distal one-quarter portion of the bud is red, nearest to a mixture of RHS 50B and 50C; the middle portion is yellow-green, nearest to RHS 145C; and, the proximal one-third portion of the bud is yellow-green, nearest to RHS 144B.

Flower:

*Flowering habit.*—Moderately free flowering.

*Shape.*—Funnelform.

*Flower vertical height.*—8.6 cm.

*Flower width.*—8.6 cm.

*Flower length.*—7.5 cm.

*Diameter of floral throat.*—2.2 cm, at its widest point.

*Floral throat texture.*—Glabrous; smooth.

*Diameter of floral tube.*—2.3 cm at the distal end; at approximately one-third of the distance from the base, where tube begins to widen, the diameter is 0.4 cm.

*Length of floral tube.*—6.0 cm.

*Floral tube texture.*—Glabrous; smooth.

*Aspect.*—Flowers are outward facing.

*Fragrance.*—A faint pleasant fragrance; acidic-sweet.

*Lastingness.*—Approximately 10 days.

*Persistent.*—Self-cleaning.

*Pedicels.*—Dimensions — 2.5 cm long and 0.25 cm in diameter. Aspect — Upward and outward; approximately 20 degrees to the peduncle axis. Strength — Moderately strong. Texture and luster — Glabrous, smooth, and moderately glossy. Color — Yellow-green, nearest to in between RHS 146C and 146D, and strongly suffused with greyed-orange, nearest to RHS 172C.

*Petals.*—Quantity of Petals — 5. Arrangement — Single whorl; petals imbricate and fused into an elongated tube at the base; lower two-thirds of the petals are fused. Shape of petal lobes — Spatulate. Dimensions, free portion of petals — 9.6 cm long and 4.0 cm wide. Apex — Unequal short apiculate. Base — Truncate; fused at the base. Margin — Entire; moderately undulated. Aspect — Somewhat reflexed. Pubescence, texture and luster of inner surface — Glabrous, velvety and matte. Pubescence, texture and luster of outer surface — Glabrous, moderately velvety and slightly glossy. Petal lobe color when opening, inner surface — Red, nearest to RHS N45B. Petal lobe color when opening, outer surface — Red-purple, nearest to RHS 69D, and fading darker towards the floral tube, nearest to a mixture of RHS 58A and 58B. Petal lobe color when fully opened, inner surface — Red, nearest to in between RHS N45B and 53A; narrowly margined white, nearest to RHS 155D. No visible venation. Color do not fade with age. Petal lobe color when fully opened, outer surface — Red-purple, nearest to RHS 69D, and fading darker towards the margins, nearest to a mixture of RHS 58A and 59D. No visible venation. Colors do not fade with age. Floral throat color — Red-purple, nearest to RHS 58B. Floral throat venation color — No visible venation. Inner corolla tube color, when fully opened — Red, nearest to RHS 54B, and fading to orange-red towards the base, nearest to RHS 34B; narrow portion of the tube is yellow-green, nearest to RHS N144B. Veins at the point of flower petal fusion are yellow, nearest to RHS 13B; all other veins are red-purple, nearest to RHS 58B. Outer corolla tube color, when fully opened — Red-purple, nearest to a mixture of RHS 69A and 69B, and fading to yellow-green towards the narrow portion of the tube, nearest to RHS 151D; narrowest portion of the tube is greyed-orange, nearest to RHS 175B. No visible venation.

*Calyx.*—Shape — Rotate; single whorl of sepals. Dimensions — 0.5 cm in diameter and 0.9 cm long.

*Sepals.*—Arrangement — Sepals are free, rotate. Quantity — 5. Shape — Narrow triangular to lanceolate. Sepal dimensions — 0.8 cm long and 0.175 cm wide at the base. Apex — Narrow acuminate. Base — Cuneate. Margin — Entire; not undulated. Pubescence, texture and luster, upper surface — Smooth; glabrous; slightly glossy. Pubescence, texture and luster, lower surface — Smooth; glabrous; very slightly glossy. Color when opening, upper surface — Yellow-green, nearest to RHS 145C; apex is greyed-red, nearest to RHS 180D. Color when opening, lower surface — Yellow-green, nearest to RHS 145C; apex is greyed-red, nearest to RHS 180C. Color when fully opened, upper surface — Yellow-green, nearest to RHS 145B; apex is greyed-red, nearest to RHS 180C. Color when fully opened, lower surface — Yellow-green, nearest to RHS 145B; apex is greyed-red, nearest to RHS 180C.

Reproductive organs:

*Androecium.*—Stamen quantity — 5. Attachment — Adnate. Filament length — 0.4 cm. Filament color — Yellow-green, nearest to RHS 151B; filaments are densely pubescent with short hairs colored white, RHS 155D. Anther attachment — Basifixed. Anther shape — Narrow sagitate. Anther length — 1.0 cm. Anther width — 0.15 cm. Anther color — Greyed-yellow, nearest to RHS 162C. Anther aspect — The five anthers are touching at their apices, thus forming a cone of anthers. Pollen, presence — None detected.

*Gynoecium.*—Pistil quantity — One. Pistil length — 2.4 cm. Style length — 2.2 cm. Style color — Yellow-green, nearest to RHS 145D. Stigma shape — Club-shaped. Stigma length — 0.2 cm.

Stigma diameter — 0.3 cm. Stigma color — Yellow-green, nearest to RHS 151D. Ovary color — Green, nearest to RHS 143C.

Seed and fruit: None observed.

Comparisons with the Parent Plants

The true parentage of the claimed plant is unknown. Therefore, no comparisons are available.

Comparison with the Most Similar *Mandevilla* Cultivar Known to the Inventor

Plants of the new cultivar 'PATMANROS5' differs from the commercial variety, *Mandevilla* 'PATMANROS3' (U.S. patent applicant Ser. No. 17/239,230), in the following characteristics described in Table 1 below.

TABLE 1

| Characteristic | 'PATMANROS5' | 'PATMANROS3' |
|---|---|---|
| Growth habit. | Less branching and less densely foliaged than 'PATMANROS3' | More free branching and more densely foliaged than 'PATMANROS5'. |
| Flower size. | Larger than 'PATMANROS3'. | Smaller than 'PATMANROS5'. |
| General coloration of the outer corolla when fully opened. | Very light red-purple and becoming considerably darker towards the margins. | Very light red-purple and becoming somewhat darker towards the margins. |
| General coloration of the inner corolla when fully opened. | Dark red-purple, generally appearing as a deep pink coloration, and narrowly margined white. | Light red-purple, generally appearing as a light pink coloration. |

That which is claimed is:

1. A new and distinct variety of *Mandevilla* plant named 'PATMANROS5', substantially as described and illustrated herein.

* * * * *